United States Patent [19]
DiLeo

[11] 4,050,055
[45] Sept. 20, 1977

[54] ATTENUATOR CIRCUIT ULTRASONIC TESTING

[75] Inventor: Christopher C. DiLeo, Brewster, N.Y.

[73] Assignee: Krautkramer-Branson, Incorporated, Stratford, Conn.

[21] Appl. No.: 708,556

[22] Filed: July 26, 1976

[51] Int. Cl.² .............................................. G01S 9/66
[52] U.S. Cl. .................. 340/1 R; 73/67.8 R
[58] Field of Search ...................... 340/1 R, 3 A, 5 C; 73/67.8 R, 67.9

[56] References Cited

U.S. PATENT DOCUMENTS

| 3,553,636 | 1/1971 | Baird | 340/1 R |
| 3,738,159 | 6/1973 | Donnadieu | 73/67.9 |

*Primary Examiner*—Richard A. Farley
*Attorney, Agent, or Firm*—Ervin B. Steinberg; Philip J. Feig

[57] ABSTRACT

A broad bandwidth, constant input impedance programmable attenuator circuit for use in pulse-echo ultrasonic testing is provided for attenuating an acoustic discontinuity responsive electrical signal. The attenuator circuit is programmable either by computer or manually and comprises solid state components, specifically a constant current source and unidirectional current conducting devices. The attenuator circuit exhibits both constant input impedance over a wide range of operating frequencies and immunity from varying output load conditions.

13 Claims, 5 Drawing Figures

ATTENUATOR CIRCUIT ULTRASONIC TESTING

BRIEF SUMMARY OF THE INVENTION

This invention concerns a broad bandwidth, constant input impedance programmable attenuator circuit for use in pulse-echo ultrasonic testing and more specifically discloses an attenuator circuit for attenuating an echo responsive electrical signal, by a predetermined value, which value is programmable either manually or automatically, for instance by computer.

In a pulse-echo ultrasonic test apparatus a pulse generator periodically provides trigger signals to an electroacoustic transducer probe. The probe acoustically coupled via water, oil, or other suitable couplant to the surface of a workpiece, responsive to the receipt of the trigger signal, transmits an ultrasonic search signal into the workpiece. A portion of the ultrasonic search signal upon intercepting an acoustic discontinuity in the workpiece is reflected back toward the probe whereat the reflected ultrasonic signal is converted into an echo responsive electrical signal. The electrical echo responsive electrical signal is then conducted via an attenuator circuit to a receiver circuit for indicating the magnitude of the signal. Since pulse-echo testing essentially is a comparison method of testing, the attenuator usually is adjustable in predetermined increments to evaluate the magnitude of the echo responsive signal by determining whether such signal is greater or smaller than a predetermined standard defect available from a calibration block. Typically, the signal from a defect is determined to be larger or smaller than a signal from a known defect in a calibration block in units of decibel (db).

In prior art attenuator circuits, Pi-section circuits and mechanical switches have been used. The Pi-section circuit requires the selection of reactive components exhibiting substantially constant electrical impedance over a wide range of frequencies. Such component selection being critical, the expense and complexity of the circuit is unduly increased. Moreover, operation of mechanical switches is relatively slow and switches need to be replaced after a finite number of operations.

The present invention utilizes the resistive voltage dividers employing components which exhibit constant input impedance over the desired operating frequency band. Solid state switching means replace the mechanical switches, thus providing faster operation and an extremely long useful component life. Solid state circuitry allows the use of high density packaging techniques, thereby reducing the quantity and size of the components used in such an attenuator circuit. In addition, solid state programming means, such as a programmable read only memory (PROM), are incorporated into the present circuit to facilitate computer programmed attenuation. For example, a computer programmed for providing amplification data can evaluate an echo responsive signal and provide a signal to the PROM for properly attenuating the subsequently received echo responsive electrical signal.

Precision current sources are provided to bias unidirectional current conductive means, e.g. diodes, which are matched to assure constant input impedance and constant programmed attenuation of the attenuator circuit over the operating frequency band.

A further prior art difficulty in attenuator design has been the effect of load variations upon the output stage of the attenuator circuit. In the present embodiment, a low capacitance switch connected in series with a high impedance device shunting the output stage provides the final attenuation stage for the echo signal.

In a preferred embodiment of the present invention selective attenuation of the echo responsive electrical signal from 0 to 49 decibels in increments of one decibel is provided. Moreover, the circuit bandwidth response extends over a frequency range of at least twenty Megahertz.

A principal object of this present invention, therefore, is the provision of a new and improved attenuator circuit useful in pulse-echo ultrasonic testing.

A further object of this invention is the provision of a novel attenuator circuit for an ultrasonic test apparatus, the attenuator circuit exhibiting a constant input impedance at frequencies up to twenty Megahertz.

A further object of this invention is the provision of an attenuator circuit having a novel output stage including a low capacitance switch connected in series with a high impedance device for reducing the adverse effect of loading upon the attenuation circuit.

A still further object of this invention is the provision of a solid state attenuator circuit, such circuit being programmable for providing a predetermined attenuation of an echo responsive electrical signal.

Another object of this invention is the provision of a programmable digital attenuator circuit programmable by a computer.

Further and still other objects of the present invention will become more clearly apparent when the following specification is read in conjunction with the accompanying drawings.

DETAILED DESCRIPTION OF THE INVENTION

Figure 1:
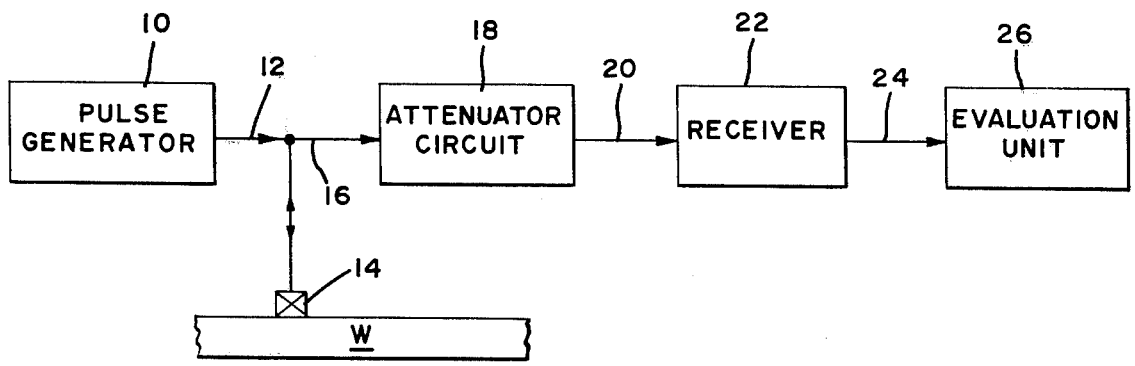
FIG. 1 is a schematic electrical block diagram of a typical pulse-echo ultrasonic test circuit.

Referring to the figures and FIG. 1 in particular, a schematic block diagram of an ultrasonic pulse-echo test arrangement is shown. A pulse generator 10 periodically provides trigger signals along conductor 12 to an electroacoustic transmit-receive transducer probe 14. The probe 14, acoustically coupled via water, oil or other suitable couplant to a workpiece W, transmits ultrasonic search signals into the workpiece responsive to the receipt of a trigger signal. A portion of the search signal upon intercepting an acoustic discontinuity, such as the entrant surface, rear surface, or a defect disposed in the workpiece, is reflected back toward the probe 14. The probe 14, in turn, converts the reflected acoustic echo signal into an echo responsive electrical signal. The echo responsive electrical signal is conducted from the probe 14 via conductor 16 to an attenuator circuit 18. The attenuated echo responsive signal is provided from attenuator circuit 18 via conductor 20 to receiver 22 and via conductor 24 to an evaluation unit 26 for defect signal processing in a manner well known in the art. It is of course well understood that a preamplifier circuit (not indicated) can be disposed in the echo responsive signal path between the probe 14 and the attenuator circuit 18 without affecting the basic operation of the described test arrangement.

Figure 2:
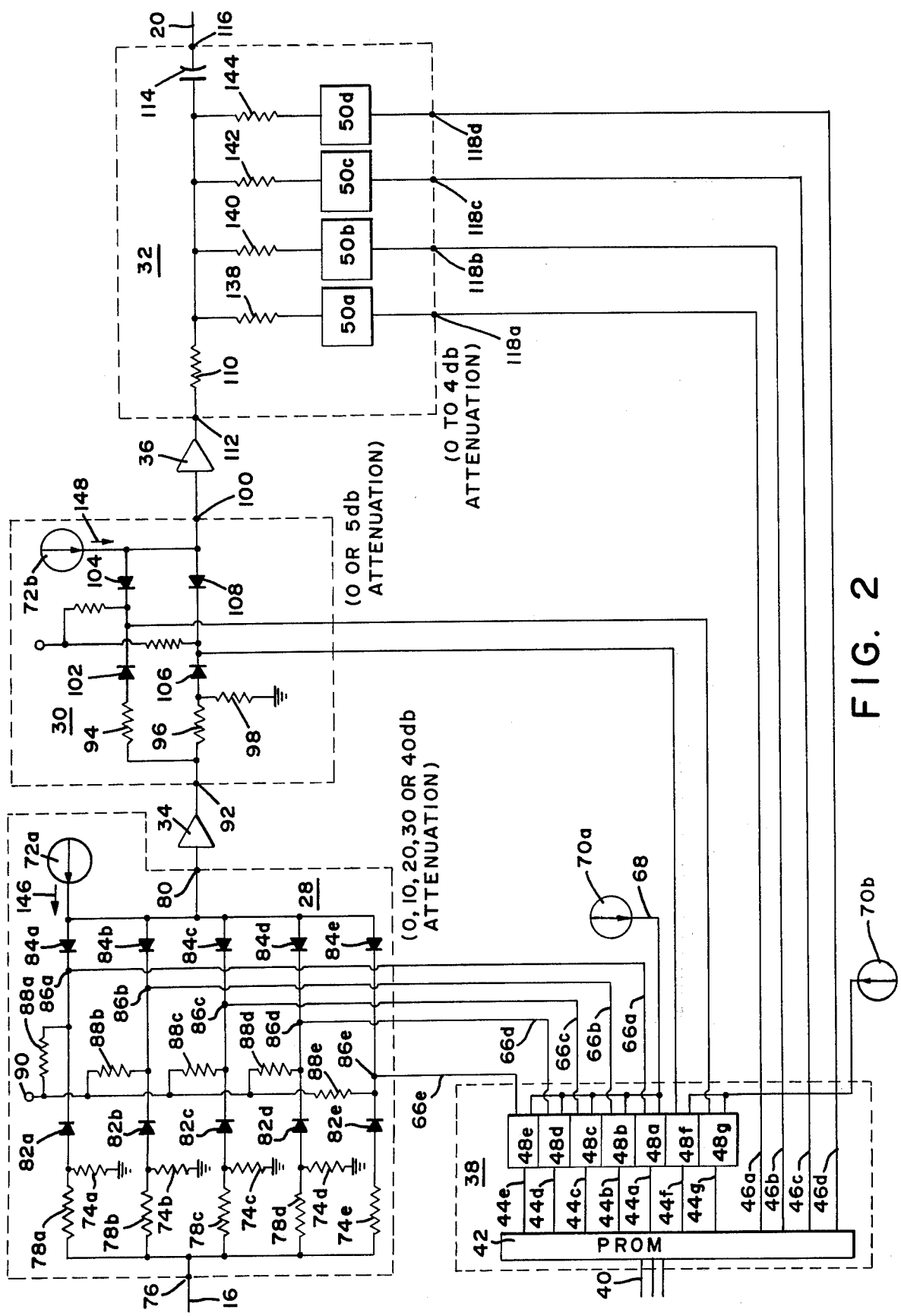
FIG. 2 is a schematic electrical circuit diagram of a preferred embodiment of the invention.

FIG. 2 is a preferred embodiment of the attenuator circuit 18 comprising the present invention. The attenuator circuit 18 comprises three serially coupled attenuator network sections 28, 30 and 32, each section being isolated from the other via a buffer amplifier 34 and 36, e.g. a transistor emitter follower circuit. The attenuator circuit networks 28, 30 and 32 are controlled by a processor 38 for providing the desired signal attenuation as will be explained hereinafter. The signal along conductors 40 is derived in a preferred embodiment from a computer, but the signal alternatively can manually be selected via a potentiometer, thumbwheel switches or the like for providing digital attenuation of the signal.

The processor 38 comprises a PROM 42 or other decoding means which decodes the input signal provided along conductors 40 for causing output signals along selected conductors 44a-g and 46a-d to be transmitted to associated switches 48a-g and 50a-d for causing selected switches to be rendered conductive.

Switches 48a-e are connected to attenuator circuit network 28 and switches 48f and 48g are connected to attenuator circuit network 30 for providing control signals to the respective networks. The switches comprise a transistor array, such as an RCA device CA3183E.

Figure 3:
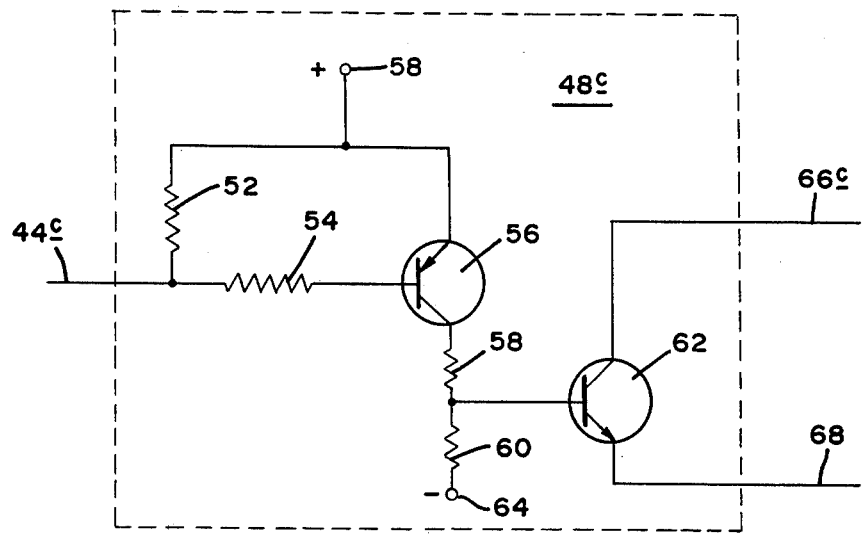
FIG. 3 is a schematic electrical circuit diagram of a portion of the circuit per FIG. 2.

The construction of each switch is identical and will be described in conjunction with switch 48c. As best seen in FIG. 3, conductor 44c from PROM 42 is connected respectively to one end of resistor 52 and resistor 54. The other side of resistor 52 and the emitter electrode of a pnp transistor 56 are connected to a positive potential voltage at terminal 58. The other side of resistor 54 is connected to the base electrode of transistor 56. The collector electrode of transistor 56 is connected to resistor 58. The other side of resistor 58 is connected to one side of resistor 60 and the base electrode of npn transistor 62. The other side of resistor 60 is connected to negative potential voltage at terminal 64. The collector electrode of transistor 62 is connected via conductor 66c to the network 28 and the emitter electrode of transistor 62 is connected via conductor 68 to a constant current source 70a, FIG. 2.

Responsive to an appropriate input signal along conductors 40, a signal transmitted from PROM 42 along conductor 44c to switch 48c is level translated by transistor 56 and its associated circuitry for causing transistor 62 to be rendered conductive. The switch 48c translates the logic level signal transmitted by PROM 42 into a voltage signal which is compatible with the attenuator circuit network 28 for coupling the network 28 via transistor 62 rendered conductive to the constant current source 70a.

The constant source 70a is connected to the emitter electrodes of transistors 62 in each switch 48a-e. Moreover, a second current source 70b identical in construction to constant current source 70a is connected to the emitter electrodes of transistors 62 in switches 48f and 48g. The current sources 70a and 70b cause current to flow through the selected conducting switches of the switch 48a-g array.

Attenuator circuit networks 28 and 30 are substantially identical and will be described in conjunction with the attenuator circuit network 28. Network 28 comprises a constant current source 72a and a plurality of parallel connected impedance circuits. Each impedance circuit includes a first resistor, e.g. resistors 74a-e, selected for providing a constant input impedance (such as 50 ohms) of the attenuator circuit 18 over a broad range of frequencies. The path including resistor 74e does not provide attenuation of the input signal manifest at terminal 76 of attenuator 18. In the remaining parallel paths a second resistor 78a-d is serially connected between input terminal 76 and the constant impedance resistor 74a-d. The resistor 78a-d are selected for providing the desired attenuation of the input signal. The ratio of the resistance of the second resistor 78a-d to the sum of the resistances of the respective first resistor 74a-d and the associated second resistor 78a-d is selected to provide the desired signal attenuation of the particular path. In the present example, the parallel paths provide 0, 10, 20, 30 or 40 db attenuation whereby the value of resistors 78a-d are selected to be 4990 ohms, 1540 ohms, 453 ohms and 107 ohms respectively.

Connected to the junction of the two resistors and to the other side of resistor 74a are an associated pair of unidirectional current conductive means coupled in opposition to the output terminal 80 of network 28. The unidirectional current conductive means comprises matched diodes 82a-e and 84a-e. Each respective diode 82a-d is connected to the junction of the associated pair of resistors 74 and 78. The cathode of each diode 82a-e is serially connected to the cathode of the associated diode 84a-e at junctions 86a-e. The anode of each diode 84a-e is connected to the signal output terminal 80. Also connected at each junction 86a-e is an associated first side of resistor 88a-e and a respective conductor 66a-e from switches 48a-e respectively. The other side of each resistor 88a-e is connected to a positive voltage potential at terminal 90. The output of constant current source 72a is coupled to the connection of the anodes of diodes 84a-e.

The series connected diodes are selected to be matched diodes exhibiting constant operating characteristics over a broad band of frequencies. In the preferred embodiment, the diodes are type 5082-2826 manufactured by Hewlett-Packard Company.

Network 30 is substantially the same as network 28 but the attenuation of the signal at input terminal 92 of network 30 is either 0 db when signal travels the path including resistor 94 or 5 db when signal is attenuated by the combination of resistors 96 and 98 connected as described in conjunction with resistors 78 and 74 in network 28. A further respective pair of unidirectional current conductive means 102, 104 and 106, 108 is connected between resistor 94 and terminal 100, and between the junction of resistors 96 and 98 and terminal 100 respectively. A constant current source 72b is connected to output terminal 100, all as described in conjunction with network 28.

Figure 4:
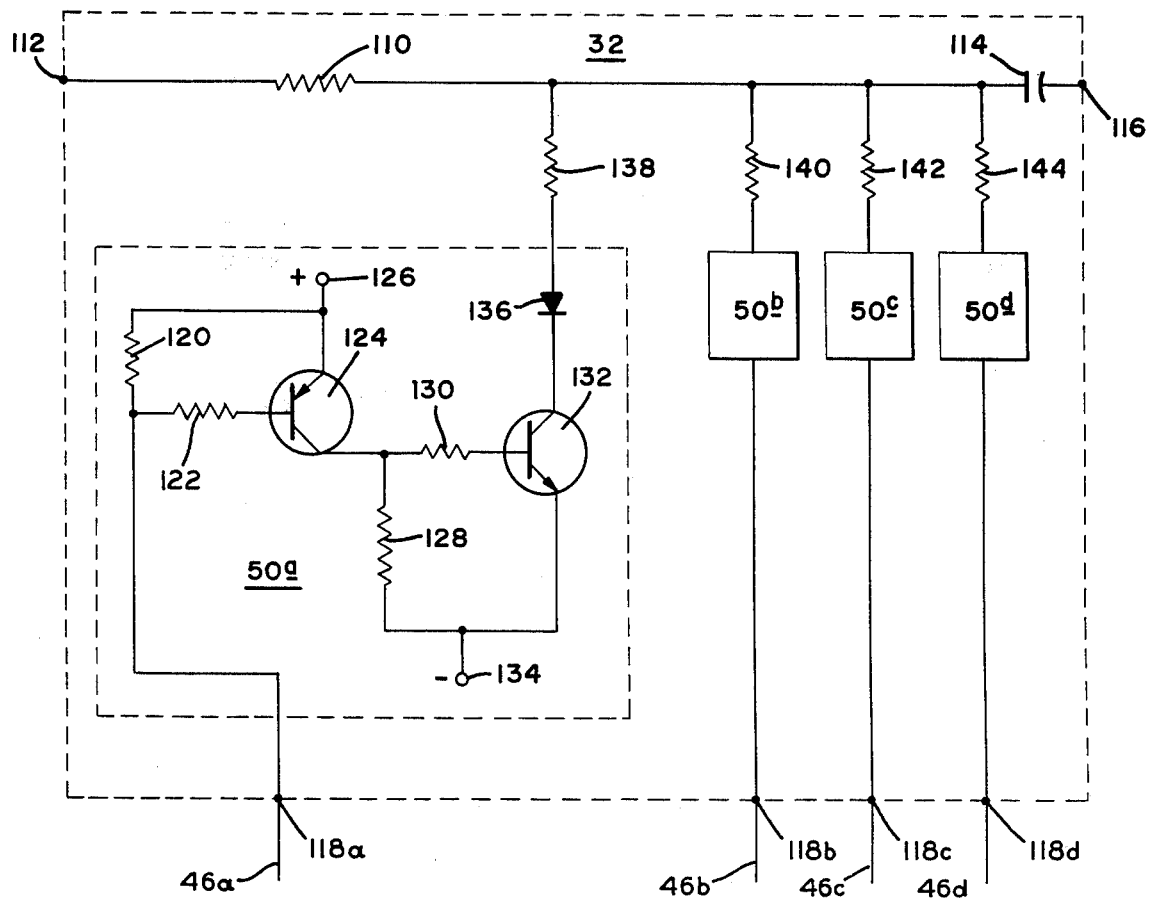
FIG. 4 is a schematic electrical circuit diagram of the output stage of the circuit per FIG. 2.

The construction of attenuator circuit network 32 is best seen with reference to FIG. 4. The network 32 comprises a resistor 110 connected at one end to input terminal 112. The other end of resistor 110 is connected to a plurality of impedance division circuits and one side of capacitor 114. The other side of capacitor 114 is connected to output terminal 116 of attenuator circuit 18 and conductor 20.

Each impedance division circuit comprises a respective serially connected high impedance and low capacitance high speed switch 50a-d. The construction of each of the switches 50a-d is identical and will be described in conjunction with switch 50a per FIG. 4. Conductor 46a connected to input terminal 118a couples a signal from PROM 42 to switch 50a. One side of resistor 120 and one side of resistor 122 are connected to terminal 118a. The other side of resistor 120 is connected to the emitter electrode of pnp transistor 124 and to a positive potential at terminal 126. The other side of resistor 122 is connected to the base electrode of transistor 124. The collector electrode of transistor 124 is connected to one end of resistor 128 and one side of resistor 130. The other side of resistor 128 and the emitter electrode of npn transistor 132 are connected to a negative voltage potential at terminal 134. The other side of resistor 130 is connected to the base electrode of transistor 132. The collector electrode of transistor 132 is connected to the cathode of diode 136. The anode of diode 136 is serially connected to one side of resistor 138 the other side of resistor 138 being connected to resistor 110.

Diode 136 is selected to be a low capacitance, high speed diode such as a hot carrier type 5082-2826, manufactured by Hewlett-Packard Company. Transistor 132 is rendered conductive responsive to a signal transmitted along conductor 46a. The effective collector electrode to emitter electrode capacitance of transistor 132 in series with the low capacitance of diode 132 is low for increasing the switching speed of the transistor 132.

Resistor 138 is selected for providing that the ratio of the resistance of resistor 138 to the sum of the resistances of resistors 110 and 138 provides the desired attenuation. Moreover, the resistance of resistor 138 is selected such that the high constant impedance of resistor 138 over the operating frequency range minimizes and makes negligible the changes of the serially connected variable low impedances of diode 136 and the collector electrode to emitter electrode impedance of transistor 132.

Switch 50a is rendered conductive for causing a one db attenuation of the signal at terminal 112 of network 32. Switches 50a and 50b are rendered conductive to cause a two db attenuation of the signal at terminal 112. Thus, resistor 140 is selected so that the parallel combination of resistors 138 and 140 in combination with resistor 110 causes the desired two db attenuation. Switch 50c is also rendered conductive for three db attenuation of the signal and all the switches are rendered conductive for a four db attenuation. For a zero db attenuation of the signal at terminal 112, all the switches remain non-conducting. In the preferred embodiment, resistors 110, 138, 140, 142, and 144 have the values 150 ohms, 1240 ohms, 1100 ohms, 976 ohms and 866 ohms, respectively.

The resistor values selected for resistors 138, 140, 141 and 144 cause the current through each conducting switch to be approximately identical resulting in substantially simultaneous operation of the switch 50a-d. In prior circuits, only one switch is rendered conductive for each desired attenuation and the current through the four db attenuation switch is approximately four times as great as the current through the one db switch. The result had always been that the higher conducting switch becomes non-conductive after the lower current conducting switch becomes conductive, thereby adversely affecting the attenuation of the signal. The present invention overcomes this prior art limitation.

Moreover, the combination of a high impedance and low capacitance impedance division network minimizes the effect of changing output load conditions upon the attenuator.

OPERATION OF ATTENUATOR CIRCUIT.

The operation of the attenuator circuit 18 will now be described in detail for a typical attenuation of 21 db.

A coded signal along conductors 40 provided either from a computer or manually is transmitted to PROM 42 contained in processor 38. The PROM 42 decodes the signal causing an output signal to be manifest along conductors 44c, 44g and 46a.

Figure 5:
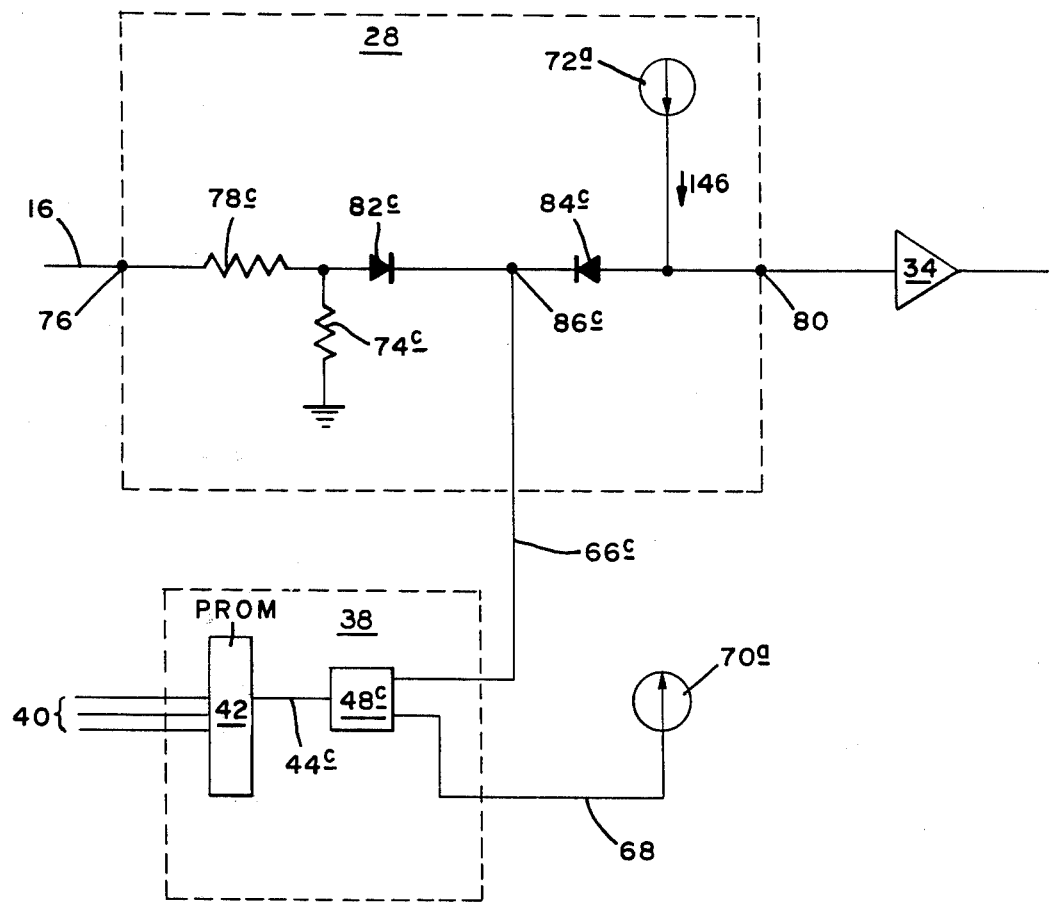
FIG. 5 is a schematic electrical circuit diagram of a portion of the circuit per FIG. 2.

The echo responsive electrical signal from probe 14 conducted along conductor 16 to input terminal 76 (FIG. 5) of attenuator circuit 18 travels through the proper parallel impedance circuit, as described below, thereby being attenuated in network 28 by 20 db. Switch 48c is rendered conductive by the signal along conductor 44c. Constant current source 72a provides a fixed current $I_1$ in the direction of arrow 146, which current passes through conducting diode 84c, to junction 86c, along conductor 66c, through switch 48c and into constant current source 70a. Constant current source 70a is designed to receive a current equal to twice the current $I_1$. Thus, a fixed current equal to $I_1$ must be conducted through matched conducting diode 82c in network 28, to junction 86c, along conductor 66c, through conducting switch 48c into constant current source 70a.

The flow of equal currents through the matched diodes 82c and 84c assures that the voltage drop and impedance characteristics of the two diodes are substantially identical.

Referring to FIG. 2 the echo responsive signal along conductor 16 is transmitted from terminal 76 through resistor 78c whereat the combination of resistors 78c and 74c attenuate the signal by 20 db. The attenuated signal is subsequently conducted through both conducting diodes 82c and 84c to terminal 80 of network 28. The attenuated signal then is transmitted to the input of a buffer amplifier 34, typically a transistor emitter follower circuit, from which amplifier the signal is transmitted to input terminal 92 of network 30.

Switch 48g is rendered conductive responsive to the signal along conductor 44g from PROM 42. Constant current source 72b provides a current of value $I_1$ in the direction of arrow 148 through conducting diode 104, and switch 48g to constant current source 70b. The constant current source 70b is designed to receive a current equal to twice $I_1$. Thus, a current equal to value $I_1$ is conducted also through diode 102, switch 48g to constant current source 70b.

The signal at terminal 92 is transmitted through the parallel impedance circuit comprising resistor 94 and oppositely connected diodes 102 and 104 to output terminal 100 without further attenuation of the signal network 30. Alternatively, had an additional 5 db attenuation of the signal been desired, the signal at terminal 92 of network 30 would have been conducted through the parallel impedance path comprising resistors 96 and 98.

The 20 db attenuated signal now apparent at terminal 100 is provided to the input of buffer amplifier 36, typically a transistor emitter follower circuit, from which amplifier the signal is provided to input terminal 112 of network 32.

Switch 50a is rendered conductive responsive to the signal transmitted along conductor 46a from PROM 42. The signal at terminal 112 is attenuated by one db by the combination of resistor 110 and the resistance of impedance division circuit comprising resistor 138 and the resistance of switch 50a.

The signal attenuated by a combined total of 21 db is coupled via capacitor 114 to the output terminal 116 of attenuator 18. The attenuated signal is transmitted from attenuator 18 via conductor 20 to receiver 22.

Responsive to a new coded signal along conductor 40, a different selected combination of switches 48a–g and 50a–d is rendered conducting and thus a signal at input terminal 76 of attenuator 18 may be attenuated by any attenuation in the range between 0 to 49 db in step of one db by traversing selected parallel impedance circuit paths and further impedance division circuits providing "fine" attenuation of the signal in network 32. The signal manifest at output terminal 116 is attenuated by a predetermined number of decibels for being further processed by receiver circuit 22 and evaluation unit 26.

While in FIG. 2 switches 50a–d are shown as forming a part of network 32, it will be apparent that these low capacitance high speed solid state switches may be placed alternatively in the processor 38, directly in the output side from PROM 42.

What is claimed is:

1. A pulse-echo ultrasonic apparatus including an attenuating means disposed in the electrical signal path from a transducer probe to a receiver circuit, said attenuating means comprising in combination;
    input terminal means and output terminal means;
    a signal attenuating network having a plurality of parallel connected impedance circuits coupled between said input terminal and output terminal means;
    each of said impedance circuits comprising attenuating means and a pair of in-opposition connected unidirectional current conductive means;
    constant current means coupled to each of said impedance circuits, and
    control means which includes further constant current means and switch means coupled to each of said impedance circuits for causing, responsive to the selective operation of said switch means, current flow between said constant current means and said further constant current means through a respective unidirectional current conductive means of a pair of such conductive means,
    whereby to provide for the passage of an electrical signal from said input terminal means over a selected impedance circuit containing said respective current conductive means to said output terminal means.

2. A pulse-echo ultrasonic apparatus as set forth in claim 1, said attenuating means comprising a resistive voltage divider.

3. A pulse-echo ultrasonic apparatus as set forth in claim 2, each of said impedance circuits having substantially the same input impedance.

4. A pulse-echo ultrasonic apparatus as set forth in claim 3, said input impedance remaining substantially constant over a frequency range of 20 Megahertz.

5. A pulse-echo ultrasonic apparatus as set forth in claim 1, said switch means comprising solid state means.

6. A pulse-echo ultrasonic apparatus as set forth in claim 5, said switch means being responsive to a programmable read-only-memory means.

7. A pulse-echo ultrasonic apparatus as set forth in claim 1, said each respective pair of said unidirectional current conductive means comprising matched diodes.

8. A pulse-echo ultrasonic apparatus as set forth in claim 1, said apparatus including further:
    a second attenuating network coupled serially between said first stated signal attenuating network and said output terminal means, and said second attenuating network comprising in combination:
    a constant impedance connected in the electrical signal path from said first stated attenuating network to said output terminal means;
    a second plurality of parallel connected impedance circuits coupled between said output terminal means and voltage potential means, and
    second control means coupled to said impedance circuits for causing selective attenuation of an electrical signal passing from said first stated attenuating network through said constant impedance to said output terminal means.

9. A pulse-echo ultrasonic apparatus as set forth in claim 8, each of said second plurality of parallel connected impedance circuits comprising a serially connected impedance and a solid state switch.

10. A pulse-echo ultrasonic apparatus as set forth in claim 9, each of said serially connected impedance being selected for providing in combination with said constant impedance a predetermined attenuation.

11. A pulse-echo ultrasonic apparatus as set forth in claim 8, and a capacitor coupled serially between said output terminal means and said second attenuating network.

12. A pulse-echo ultrasonic apparatus including an attenuating means disposed in the electrical signal path from a transducer probe to a receiver circuit, said attenuating means comprising:
    input terminal means and output terminal means;
    a signal attenuating network having a plurality of parallel connected impedance circuits coupled between said input terminal and output terminal means;
    each of said impedance circuits comprising attenuating means and a pair of in opposition connected unidirectional current conductive means;
    constant current means coupled to each of said impedance circuits, and
    control means coupled to said signal attenuating network for providing for the passage of an electrical signal from said input terminal means over a selected impedance circuit to said output terminal means.

13. A pulse-echo ultrasonic apparatus including an attenuating means disposed in the electrical signal path from a transducer probe to a receiver circuit, said attenuating means comprising:
    a first signal attenuating network having a first input terminal means, a first output terminal means, and a first plurality of parallel connected impedance circuits coupled between said first input terminal means and said first output terminal means;
    a second signal attenuating network having a second input terminal means, a second output terminal means, and a second plurality of parallel connected impedance circuits coupled between said second input terminal means and said second output terminal means;
    a third signal attenuating network having a third input terminal means, a third output terminal means, a constant impedance coupled between said third input terminal means and said third output terminal means, and a third plurality of parallel connected impedance circuits each of which comprises a serially connected impedance and switching means coupled between said third output terminal means and voltage potential means;

buffer amplifier means coupling respectively a signal at said first output terminal means to said second input terminal means and a signal at said second output terminal means to said third input terminal means;

a respective pair of in opposition connected unidirectional current conductive means connected in each of said impedance circuits comprising said first and said second plurality of impedance circuits;

constant current means coupled to each of said impedance circuits comprising said first and said second plurality of impedance circuits;

a respective solid state switch means coupled to and associated with each of said impedance circuits comprising said first, second and third plurality of impedance circuits, and control means coupled for selectively actuating said switch means for providing current flow from said constant current means through a selected current conductive means of a respective pair in said first and in said second impedance circuits and for providing a conductive path through a selected impedance circuit of said third attenuating network to cause the passage of an electrical signal at said first input terminal means through a selected impedance circuit of said first signal attenuating network, through a second selected impedance circuit of said second signal attenuating network, and through said constant impedance in said third signal attenuating network to said third output terminal means.

* * * * *

UNITED STATES PATENT AND TRADEMARK OFFICE
CERTIFICATE OF CORRECTION

PATENT NO. : 4,050,055
DATED : September 20, 1977
INVENTOR(S) : CHRISTOPHER C. DILEO It is certified that error appears in the above-identified patent and that said Letters Patent are hereby corrected as shown below:

In the Title, after "CIRCUIT" insert --FOR--.

Column 8, line 13, after "said" insert --second--.

Signed and Sealed this

Twenty-seventh Day of December 1977

[SEAL]

Attest:

RUTH C. MASON
Attesting Officer

LUTRELLE F. PARKER
Acting Commissioner of Patents and Trademarks